United States Patent [19]

Aizawa et al.

[11] Patent Number: 5,132,413

[45] Date of Patent: Jul. 21, 1992

[54] SUGAR CHAIN

[75] Inventors: Akihiro Aizawa; Nobuo Shimoda; Masakazu Adachi, all of Takasaki; Katsunari Tezuka; Hideko Ishihara, both of Nagoya; Hiroyuki Hanzawa, Hachioji; Yoji Arata, Tokyo; Noriko Takahashi, Nagoya, all of Japan

[73] Assignee: Japan Immuno Research Laboratories Co., Ltd., Takasaki, Japan

[21] Appl. No.: 588,060

[22] Filed: Sep. 25, 1990

[30] Foreign Application Priority Data

Mar. 13, 1990 [JP] Japan .................................. 1-62120

[51] Int. Cl.$^5$ .......................... C07H 1/00; C08B 37/00
[52] U.S. Cl. ...................................... 536/1.1; 536/4.1
[58] Field of Search ................................. 536/1.1, 4.1

[56] References Cited

U.S. PATENT DOCUMENTS 4,849,510  7/1989  Adachi ................................. 530/395
4,851,517  7/1989  Feder et al. ........................... 536/1.1

FOREIGN PATENT DOCUMENTS 106285  4/1984  European Pat. Off. .
318030  5/1989  European Pat. Off. .
2106935  4/1983  United Kingdom .

OTHER PUBLICATIONS

Shimoda et al., J. Biochem., vol. 102 (1987), pp. 657-664.
Lloyd et al., Immunogenetics, vol. 17 (1983), pp. 537-541.
Hakomori et al., Biochem. Biophys. Res. Comm., vol. 113 (1983), pp. 791-798.
Brown et al., Bioscience Reports, vol. 3 (1983), pp. 163-170.
McKibbin et al., J. Biol. Chem., vol. 257 (1982), pp. 775-760.

Primary Examiner—Nathan M. Nutter
Assistant Examiner—Jeffrey C. Mullis
Attorney, Agent, or Firm—Oblon, Spivak, McClelland, Maier & Neustadt

[57] ABSTRACT

A sugar chain of the following formula is disclosed.

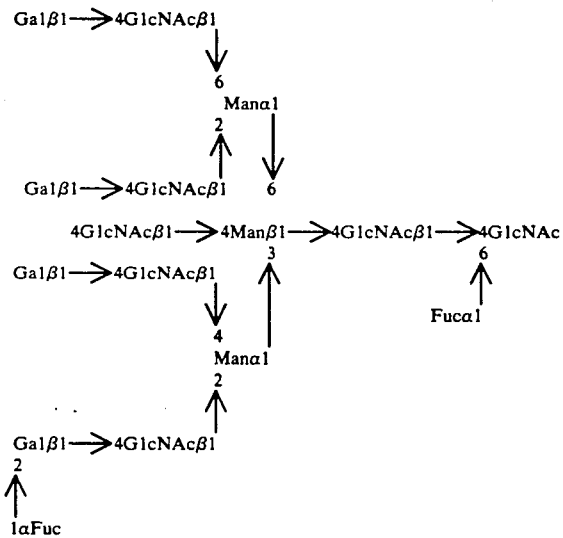

It can be prepared by separating glycoproteins from cell membrane components by using lectins which recognize the sugar chain, releasing the sugar chain structure from the glycoproteins, and purifying the released sugar chain. The sugar chain is useful for the diagnosis and treatment of cancer.

1 Claim, 10 Drawing Sheets

SUGAR CHAIN

BACKGROUND OF THE INVENTION

1. Field of the Invention

This invention relates to a novel sugar chain and, more particularly, to a novel sugar chain which is useful for the diagnosis and treatment of cancerous diseases.

2. Description of the Background Art

Sugar chains existing on cell membranes combine with proteins, lipids, and the like. They are present as glycoproteins, glycolipids, or the like widely in living bodies. Glycoproteins to which sugar chains bond play important rolls in the control of physiological functions as enzymes or hormones, or as factors for controlling osmotic pressure and the like. There are glycoproteins which function to transfer physiologically active substances such as medicines to the target organs. Thus, glycoproteins are very important substances for the living bodies. Almost all plasma proteins are said to be glycoproteins.

Blood-type antigens are known as important sugar chain antigens which are present on the surface of cells. Besides ABO (H)-type blood-type antigens which are well known in the art, there are sugar chain-containing blood-type antigens such as Lewis-type, Ii-type, and R-type [J. M. McKibbin, et a., *J. Biol. Chem.*, 257 (2), 755–760 (1982); K. 0. Lloyd, et al., *Immunogenetics*, 17, 537–541 (1983)].

Glycolipids changes in various way along with canceration of cells. Such glycolipids are therefore considered to be cancer-related cell membrane antigens. Extensive studies are ongoing for their applications to the diagnosis and treatment of cancer [A. Brown, et al., *Bioscience Reports*, 3, 163–170 (1983); S. Hakomori, *Biochem. Biophys. Res. Commun.*, 113 (3), 791–798 (1983)].

Quite a few autoantibodies which are found in autoimmune diseases recognize sugar chain antigens of itself. In this instance, the sugar chain antigens play an important role as autoantigens.

The receptors for peanut agglutinins (PNA) are confirmed to be produced in a number of human carcinomas. The present inventors have tried to clarify the sugar chain structure of the receptors as part of the studies related to the investigation in the mechanism by which the receptors are produced. As a result, the inventors could determine the structures of di- and tetrasaccharide which are the major components of O-linked sugar chains produced by an alkaline NaBH$_4$ treatment of the receptors [N. Shimoda, et al., *J. Biochem.*, 102, 657–664 (1987)].

As mentioned above, sugar chains combined with proteins and lipids have important functions in the maintenance of life in living bodies. Identification of sugar chains therefore is expected to lead to the clarification of their more definitive functions and involvements in various diseases and is considered to be useful for the diagnosis and treatment of diseases.

SUMMARY OF THE INVENTION

The present inventors have continued studies on PNA receptors and isolated a specific sugar chain having various involvements in cancer and other diseases.

Accordingly, an object of this invention is to provide a novel sugar chain (I) of the following formula,

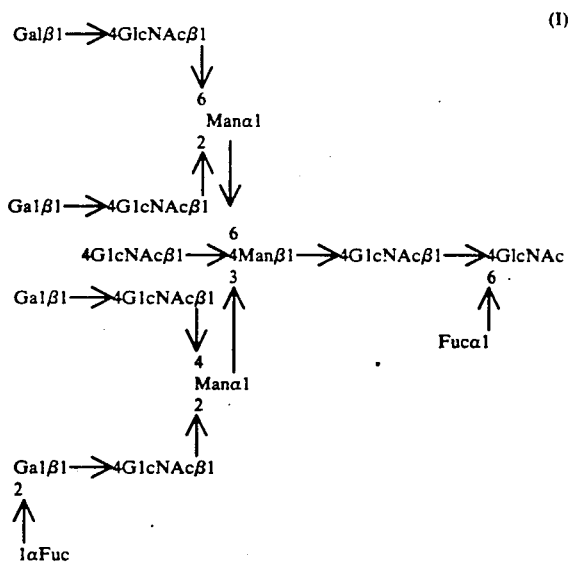

A more complete appreciation of the invention and many of the advantages thereof will be readily obtained as the same becomes better understood by reference to the following description.

DETAILED DESCRIPTION OF THE INVENTION AND PREFERRED EMBODIMENTS

Figure 1:
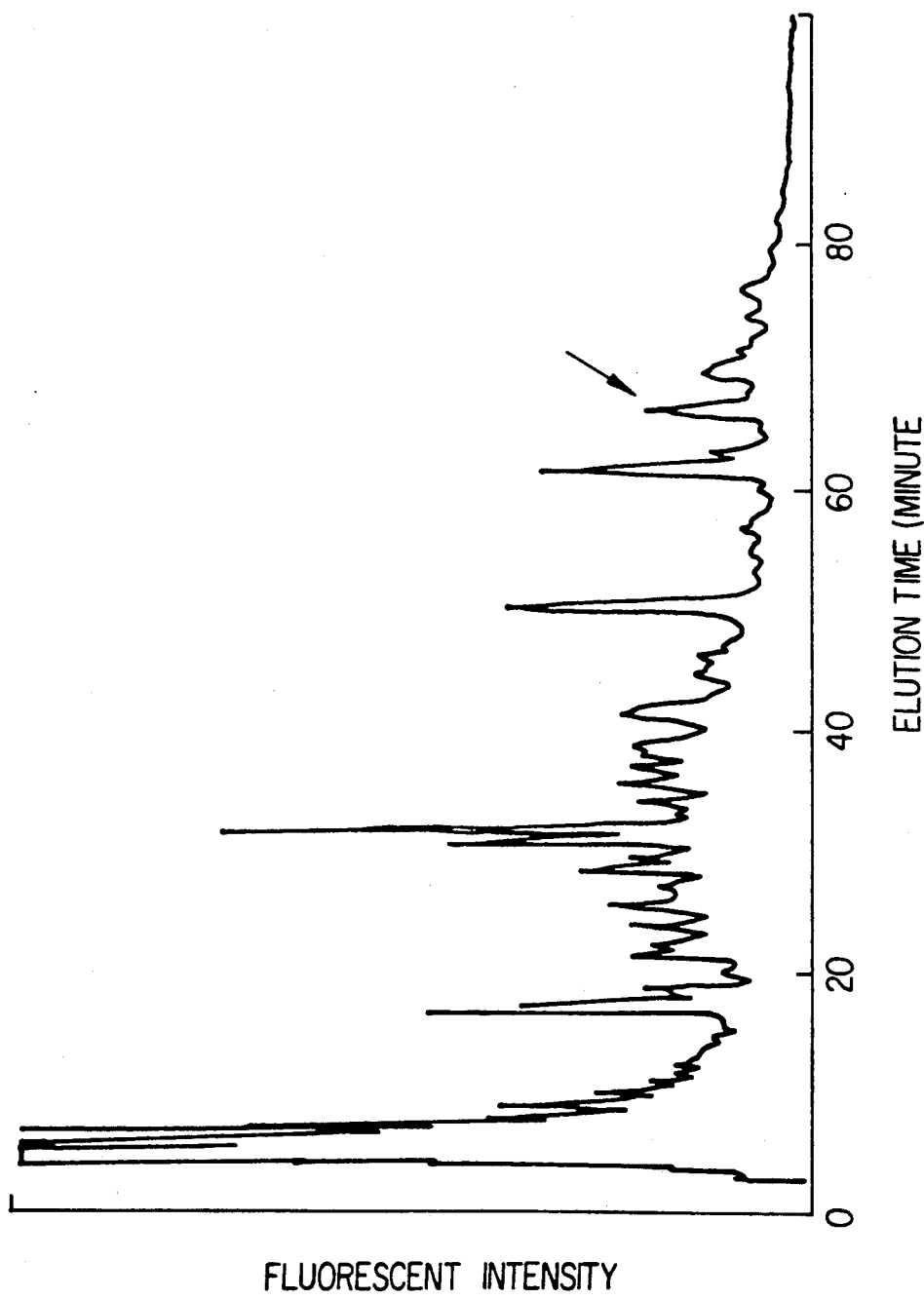
FIG. 1 shows a high performance liquid chromatography pattern of the sugar chain derivative fractions separated by an ODS-Silica column.

Sugar chain (I) of the present invention can be prepared, for example, by separating glycoproteins containing sugar chain (I) from cell membrane components by using lectins which recognize the sugar chain, releasing the sugar chain structure from the glycoproteins, and purifying the released sugar chain.

Any cells which contain the sugar chain of formula (I) can be used as a raw material. Since a large amount of cells are required for the production of the sugar chain, preferable cells are established cell strains, especially established carcinoma lines, e.g. KATO-III stomach cancer. Separation of cell membrane components from the cells can be performed, for example, by ultra-centrifugation of homogenized cells. More specifically, a suitable buffer solution, e.g. 2–10 parts by weight of a physiological saline containing phosphate buffer solution for 1 part by weight of the raw material, is charged and the cells are ground by a homogenizer or a ultra-sonic pulverizer at a low temperature. Cell membrane fractions can be obtained by ultra-centrifugation of the ground cell solution at a low temperature. It is desirable to purify the cell membrane fractions by subjecting them, after solubilization, again to ultra-centrifugation before they are submitted to the procedure for the separation of glycoproteins.

A suitable lectin is used for the separation of glycoproteins containing sugar chain (I) from the cell membrane fractions.

Any lectins which can recognize galactose, Galβl-3GalNAc, or fucose can be used for bonding the glycoproteins thereto. Examples of preferable lectins are *Arachis hypogaea* lectin (PNA), *Ricinus communis* lectin (RCA), *Lotus tetragonolobus* lectin (Lotus), *Aleuria aurantia* lectin (AAL), and the like.

Separation of glycoproteins and the like using a lectin can be performed according a conventional manner by affinity chromatography using the lectin as a ligand. Usually, polymers such as BrCN-activated sepharose, agarose, or the like can be used as a lectin carrier.

Coupling of a lectin with BrCN-activated sepharose, can be carried out, for example, by swelling a suitable amount of BrCN-activated sepharose 4B with 1 mM-HCl, thoroughly washing the swelled BrCN-activated sepharose 4B with the same HCl solution, and further washing it with a coupling buffer solution. A 0.1M carbonate buffer solution (pH 8.3) containing 0.5M sodium chloride is usually used as the coupling buffer solution. The gel washed with the coupling buffer solution is quickly added to a lectin solution (2 mg/ml) and gently shaken for 4 to 5 hours at room temperature in a shaker. The degree of the coupling during the coupling reaction can be confirmed by measuring the absorbance at 280 nm of the supernatant obtained by centrifugation (700 rpm) of samples taken before and after the initiation of the coupling reaction. When the absorbance at 280 nm becomes less than 0.01, the supernatant is discharged and the gel is washed with an addition of a glycine buffer solution, followed by shaking overnight at 4° C. in the presence of the glycin buffer solution. After that, the gel is washed three times with 400 ml of the coupling buffer solution and 400 ml of an acetate buffer solution, in turn, thus obtaining the lectin coupling sepharose.

Operation of affinity chromatography can be done according to a conventional method. The detection of the target fraction is preferably carried out using a protein as a marker.

Release of the sugar chains from the separated glycoproteins may be preferably performed, for example, by hydrazinolysis and digestion with protease, followed by digestion using glycopeptidase or the like. It is desirable that hydrazinolysis be carried out at a temperature of about 100° C. for about 5-20 hours.

Isolation of the sugar chain (I) of the present invention from the released sugar chains can be performed according to the following method. The released sugar chains are first N-acetylated, and separated into neutral sugar chains (80%) and acidic sugar chains (20%) using an ion-exchange resin. The sugar chain (I) of the present invention can be obtained by subjecting the neutral sugar chains to gel filtration, ion-exchange chromatography, and the like. A typical preferable isolation method is to submit the neutral fraction to the following separation means in the following order: (1) gel filtration, (2) pyridylamination, (3) gel filtration, (4) cationic ion-exchange chromatography, (5) gel filtration, (6) reversed phase chromatography, (7) normal phase chromatography, and (8) gel filtration.

Structural analysis of the sugar chain derivative (I) of the present invention can be carried out by means of the two-dimensional mapping technique, 1H-NMR spectrum, and methylation analysis.

Other features of the invention will become apparent in the course of the following description of the exemplary embodiments which are given for illustration of the invention and are not intended to be limiting thereof.

EXAMPLES

Example 1

Separation of cell membrane

KATO III (human signet ring cell carcinoma, stomach cancer) was cultured according to the method of Sekiguchi et al [Sekiguchi, M., et al. *Jap. J. Exp. Med.*, 48, 61–68 (1978)]in a RPMI-1640 medium containing 5% fatal calf serum. The cultured carcinoma was ground by a teflon homogenizer (manufactured by Brown Co.) with an addition of 480 ml of a physiological saline containing phosphate buffer solution (PBS) for 120 g of the cultured cells. The ground carcinoma was centrifuged at 100,000 g for 1 hour at 4° C. 180 ml of E Buffer (10 mM Tris-HCl buffer solution containing 0.85% sodium chloride, 2 mM magnesium chloride, and 2 mM calcium chloride: pH 7.6) containing 2% Triton X-100 was added to 20 g of the residue obtained by the centrifugation. After stirring for 15 minutes, the mixture was solubilized by the ultrasonic treatment in an ice-cooled bath. The solution was charged into swing-type ultra-centrifuge tubes and centrifuged at 80,000 g using SRP28-SA swing-type rotator (manufactured by Hitachi Co., Ltd.) for one and half hours at a temperature of 4° C. The uppermost fatty layer was eliminated by filtration with suction to obtain a supernatant.

Example 2

Separation of glycoproteins containing the sugar chain (I) from cell membrane fractions (a) Preparation of PNA-Sepharose 4B 400 ml of 1 mM HCl was added to about 20 g of BrCN-activated sepharose 4B (product of Pharmacia Co.) to effect swelling of the latter for 15 minutes at room temperature. The gel was washed with the same HCl solution and then 400 ml of a coupling buffer solution (0.1M carbonate buffer solution containing 0.5M sodium chloride: pH 8.3), and quickly added to 2 mg/ml PNA solution (product of Seikagaku Kogyo Co., Ltd.). The mixture was gently shaken at room temperature for 4–5 hours using a shaker (SS-80: trade name, made by Tokyo Rikakikai Co.). The gel solution was centrifuged at 700 rpm for 3 minutes. When the absorbance of the supernatant became less than 0.01 at 280 nm, the supernatant was removed. A glycin buffer solution was added to the gel and the mixture was centrifuged at 700 rpm for 3 minutes. 200 ml of glycin buffer solution was again added to the residue and the mixture was shaken overnight at 4° C. The gel solution was transferred to a glass filter, and washed with about 400 ml of the coupling buffer solution and then with about 400 ml of 0.1M acetate buffer solution containing 0.5M sodium chloride, while being filtered by suction. After repetition of the washing procedure two times, the gel was equilibrated with a 2% Triton X-100 E buffer solution.

(b) Separation by affinity chromatography 700 ml of the cell membrane fraction obtained in (1) above was added to the above column using a perista pump (ATTO SJ-1215) over a period of about 45 to 50 hours. The mixture was washed with the 2% Triton X-100 E buffer solution over a period of 24–36 hours, 0.5% Triton X-100 E buffer solution over 24–36 hours, and then 0.1% Triton X-100 E buffer solution over 24–36 hours. Elution was performed using about 250 ml of 0.1% Triton X-100 E buffer solution containing 0.2M lactose over 20-24 hours. Eluted fractions, in an amount of 200 drops each, were collected in fraction collectors. Absorbance at 280 nm was measured on each 200 droplet fraction. Fractions exhibiting a protein peak were collected and sterilized with Minisart (Minisart SM-16534: trade name, product of Sartorius Co.), took into cellophane tube for dialysis (made by Wako Pure Chemical Co., Ltd.) and dialyzed against 5,000 ml of physiological saline at 4° C. for 4-5 days, while replacing 8 times the external solution.

(c) Purification of glycoproteins (1)

To about 75 ml, an amount equivalent to 20-25 mg as proteins, of fractioned sample obtained in (b) above, were added 20 ml of 2.5M Tris-HCl buffer solution, then 1 g of SDS (sodium dodecyl sulfate, manufactured by Nakarai Tesque Co., Ltd.) to dissolution. The solution was washed with an ultrasonic bath (VS-150: trade name, manufactured by VELVO Co.) for 15 minutes at 25° C. After an addition of 5 ml of 0.5M Tris-buffer solution to which 200 mg of DDT (dithiothreitol, manufactured by Nakarai Tesque Co., Ltd.) was added, and replacement with nitrogen gas, the ultrasonic washer was sealed and allowed to stand for 12 hours at 25° C. 10 ml of 0.5M Tris-buffer solution to which 400 mg of IAA (iode acetamide, manufactured by Nakarai Tesque Co., Ltd.) was added the reaction solution and the mixture was allowed to stand for a further 1-2 hours at 25° C, after which 1 ml of a 10% Triton X-100 solution was added to it. The solution was dialyzed against 5,000 ml of a 0.1% Triton X-100 PBS solution at room temperature for 3 days, during which the external solution was replaced 3 times. All above procedures have been performed under sterilized conditions.

(d) Purification of glycoproteins (2)

The sample treated in (c]above was added to PNA-sepharose 4B column which had been equilibrated with a 0.1% Triton X-100 PBS solution using a perista pump over a period in a cold chamber kept at 4° C. The of about 16-24 hours sample was the washed with 1,000 ml of a 0.1% Triton X-100 PBS solution over 48 hours and then with about 500 ml of a 0.01% Tween 80 PBS over 24 hours, followed by elution with 100-120 ml of a 0.2M lactose 0.01% Tween 80 PBS over 24 hours to collect fraction, 50 drops each. Absorbance at 280 nm was measured for each fraction. The fractions exhibiting a protein peak were collected. The collected fractions were sterilized with Minisart, put into a dialysis tube and dialyzed against 5,000 ml of a 0.01% Tween 80 physiological saline at 4° C. for 4-5 days, while replacing the external solution 8 times. Upon completion of the dialysis, further sterilization was carried out with Minisart, and the sugar protein sample thus obtained was stored at 4° C.

(e) Isolation of the sugar chain of the present invention from the glycoprotein

About 460 ml, equivalent to 80 mg of the protein, of the purified glycoprotein, diluted with water to a 10-fold volume, was concentrated to about 5 mg/ml by an ultrafilter (Amicon M.W., 10,000 cut-off) and took into 6 test tubes ($\phi 1 \times 10$ cm) with a screwed teflon packing for liophylization, followed by a further drying in a desiccator in the presence of $P_2O_5$ and KOH under reduced pressure with heating at 45° C. for 4-5 days.

0.4 ml of hydrazine anhydride was added to each test tube, of which the opening was closed tight, and the content was reacted for 10 hours at 100° C. After cooling the test tubes to the room temperature, the hydrazine was removed by allowing the tubes in a desiccator in the presence of concentrated $H_2SO_4$ under reduced pressure overnight. An addition of several drops of toluene followed by drying to solidification was repeated until the vapor of the content became pH 8. An addition of 7 ml of saturated sodium bicabonate solution and 0.35 ml of acetic anhydride with stirring was repeated 10 times. The fractions passing through a cationic exchange resin [Dowex 50Wx8 H+ form (100-200 mesh) 70 ml] and fractions passing through the cationic exchange resin when 350 ml of water (5 times of the volume of the resin) was charged were collected and freeze-dried.

The freeze-dreid substance was dissolved into about 10 ml of water and subjected to an anionic exchange resin [AG-1×2 Acetate-form (200-400 mesh) 250 ml]. The fractions passing through the anionic exchange resin and fractions passing through the ionexchange resin when 2,500 ml of water (10-fold of the volume of the resin) was charged were collected and concentrated by an evaporator. The concentrate was dissovled into 1.5 ml of water and submitted to gel filtration [Bio-Gel P-4 ($\phi 1.5 \times 93$ cm, 164 ml, −400 mesh, 55° C.) to collect tetra- or greater polysaccharide fractions, followed by concentration to about 10 ml with an evaporator.

The concentrate was took into 34 test tubes with a screwed teflon packing and dried in a desiccator to solidify, followed by an addition of 500 $\mu l$ of 2-aminopyridine solution (* 1) to each test tube. After complete dissolution and tight sealing of the opening, the tubes are heated at 100° C. for 15 minutes. 30 $\mu l$ of a reducing solution (* 2) was added to each test tube and thoroughly mixed, followed by heating again at 90° C. for 15 minutes.

To the contents of seven test tubes which were combined together water was added to a volume of about 5 ml. Fractions in the neighborhood of those passing through Sephadex G-10 ($\phi 1.5 \times 56$ sm, 100 ml) which had been equilibrated with 10 mM ammonium bicarbonate were collected. The same procedure was performed 5 times to collect the same fractions for all 34 test tubes. The collected fractions were concentrated by an evaporator, and adsorbed to a cationic exchange resin [Dowex 50Wx2 H+ form (100-200 mesh) 320 ml]. The fractions eluted with 2,000 ml of 0.5N ammonia solution (6 times of the volume of the resin) were collected and concentrated by an evaporator. The concentrate was subjected to Sephadex G-10 ($\phi 1.0 \times 45$ cm, 35 ml) which had been equilibrated with 10 mM ammonium bicarbonate. Fractions in the neighborhood of those passing through were collected and concentrated by an evaporator. The initial buffer solution (* 3 0 for ODS-Silica column was added to the concentrate to a volume of 1.5 ml.

The sample was charged into a ODS-Silica column in 30 portions under the following conditions ( 3) to collect fractions of a peak in the neighborhood of 2 8 of glucose units, i.e., the peak indicated by an arrow in FIG. 1. After concentration by an evaporator, the initial buffer solution for an Amide-Silica column was added to make the final volume to 200 $\mu l$. The sample was then charged into an Amide-Silica column in several portions under the following conditions (* 4) to collect fractions of a peak in the neighborhood of 10.6-saccharide in glucose unit. After concentration by an evaporator, the residue was dissolved in a 10 mM ammonium bicarbonate to make the final volume to 200 μl and subjected to Sephadex G-15 (100 1.0×45 cm, 35 ml) which had been equilibrated with 10 mM ammonium bicarbonate. The fraction passing through the column was collected and dired by an evaporator to obtain the sugar chain of the present invention.

* 1 2-Aminopyridine solution:
  A solution of 1 g of 2-aminopyridine in 0.76 ml of 12n Hcl.
* 2 Reducing solution:
  A solution of 10 mg of NaBH$_3$CN in 20 μl of 2-aminopyridine solution and 25 μl of water.
* 3 ODS-Silica column HPLC conditions:
  Column: Shimpack CLC-oDS (0.6 cm×15 cm),
  Flow rate: 1.0 ml/min.
  Column temperature: 55° C.
  A Solution: 10 mM phosphate buffer (pH 3.8)
  B Solution: A solution containing 0.5% 1-butanol

| Gradient Conditions: | 0 min. → | 100 min. |
|---|---|---|
| A Solution | 80% | 30% |
| B Solution | 20% | 70% |

* 4 Amide-Silica column HPLC conditions:
  Column: TSK-GEL Amide-80 (0.46 cm×25 cm), manufactured by Tosoh Co., Ltd.
  Fow rate: 1.0 ml/min.
  Column temperature: 40° C.
  C Solution: A mixed solution of 3% acetic acid adjusted to pH 7.3 with triethylamine and acetonitrile (35:65).
  D Solution: A mixed soltuion of 3% acetic acid adjusted to pH 7.3 with triethylamine and acetonitrile (50:50).

| Gradient Conditions: | 0 min. → | 50 min. |
|---|---|---|
| A Solution | 100% | 0% |
| B Solution | 0% | 100% |

A fluorescent monitor (excitation wavelength: 320 nm; emission wavelength: 400 nm) was used for the detection of peaks of fractions separated from each column. Elution sites for each column were designated by the saccharide number based on the pyridylamino derivative elution site of dextran hydrolyzates (4 to 31 saccharide).

The results of the 1H-NMR measurement on the sugar chain of the present invention prepared above are shown in the following table.

Conditions of 1H-NMR Measurement
  Instrument: Bruker AM-400 (400 MHz)
  Temperature: 30° C. (Standard Measurement) 60° C. (For separation of HDO signal and the target signal)
  Standard material: Acetone was used as a secondary standard material. (2.216 ppm, in D$_2$O at 30° C.) (2.213 ppm, in D$_2$O at 60° C.)

TABLE 1

| $^1$H-NMR Chemical Shift Value (Anomeric-1H) | | | |
|---|---|---|---|
| | | Chemical Shift (ppm) | |
| Type | Site | Peak 1 | Remark |
| Fuc | | 4.854 | Fuc 1-6 |
| | | 5.334 | Fuc 1-2 |
| Man | 4 | 4.985 | |
| | 4' | 4.892 | |
| | 3 | (4.680) | |
| GlcNAc | 2 | (4.709) | |
| | 5 | 4.534 | |
| | 5' | 4.592 | |
| | 7 | 4.534 | |
| | 7' | 4.534 | |
| | Bisect | 4.440 | |
| Gal | 6 | (4.664) | |
| | 6' | 4.462 | |
| | 8 | 4.462 | |
| | 8' | 4.482 | |

*Measured at 30° C., except that the figures in parentheses were measured at 60° C.

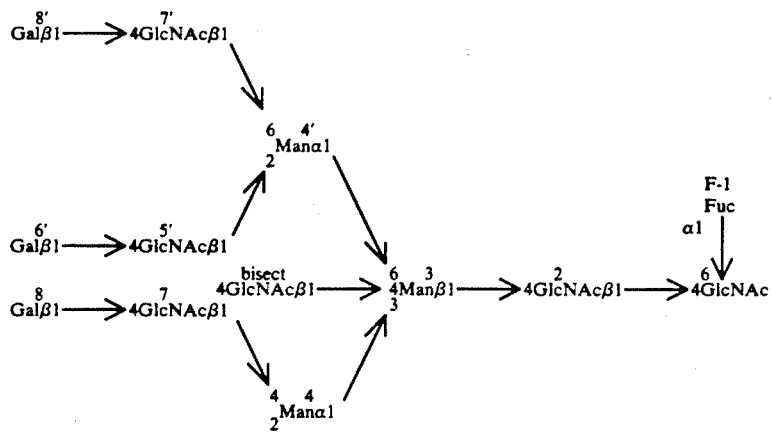

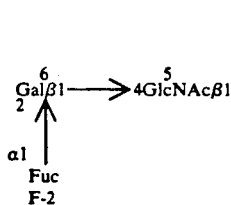

TABLE 2

| Type | Chemical Shift (ppm) Peak 1 | Remark |
|---|---|---|
| GlcNAc | 2.072 | |
| | 2.072 | |
| | 2.060 | |
| | 2.051 | |
| | 2.047 | |
| | 2.023 | |
| | 1.952 | (suggests 7 GlcNAc residues in the sugar chain) |
| Fuc | 1.151 | Fuc 1-6 |
| | 1.194 | Fuc 1-2 |

*Measured at 30° C., except that the figures in parentheses were measured at 60° C.

Methylation analysis of the sugar chain derivative was carried out under the following conditions.

Column: SP 2380 (0.53 mm×30 m), manufactured by Supelco Inc., Bellefonte, Pa.

CG-MS: JMS-DX303, manufacture by Japan Electronic Co.

Figure 2:
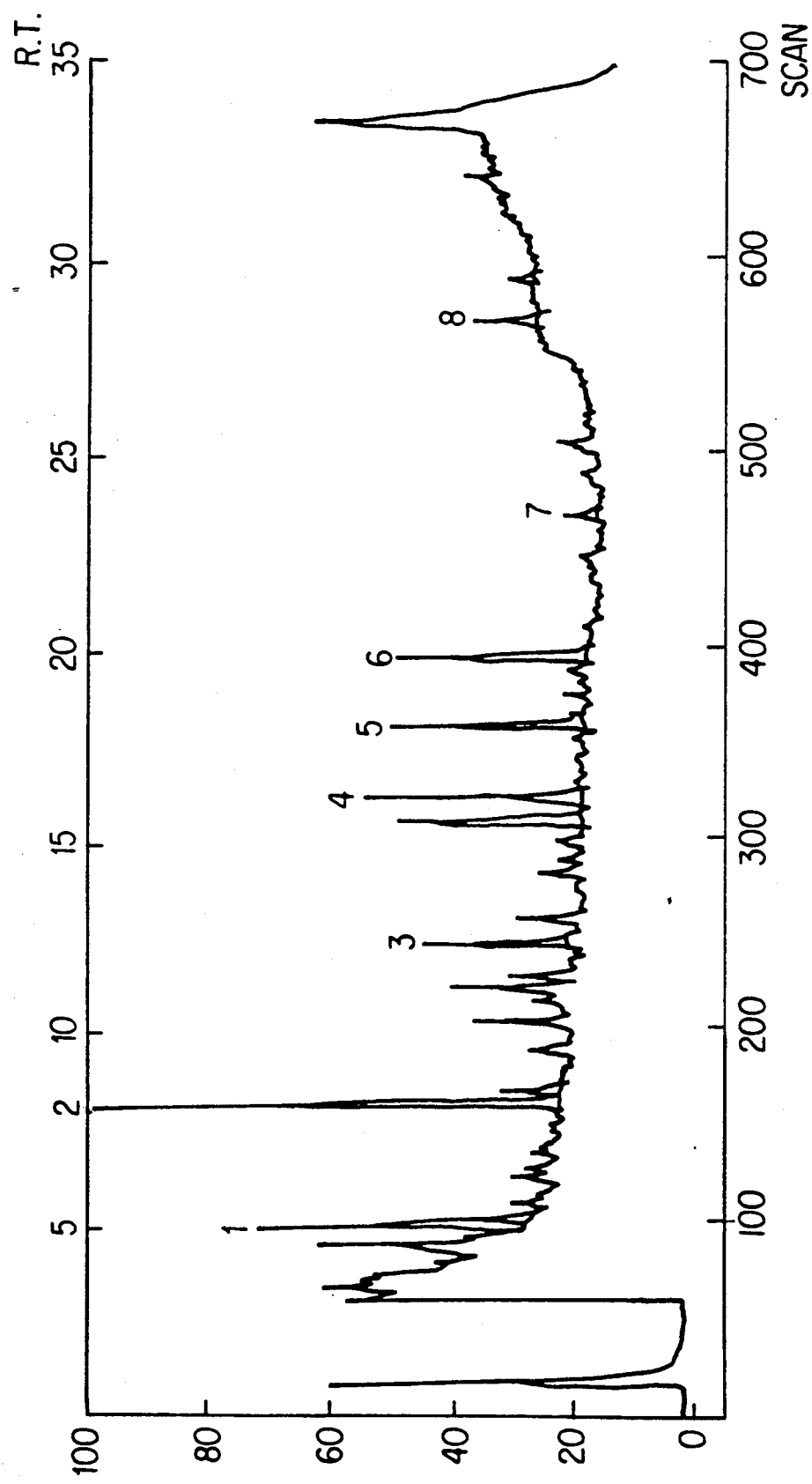
FIG. 2 is the total ion chromatograph of the sugar chain derivative.
Figure 3:
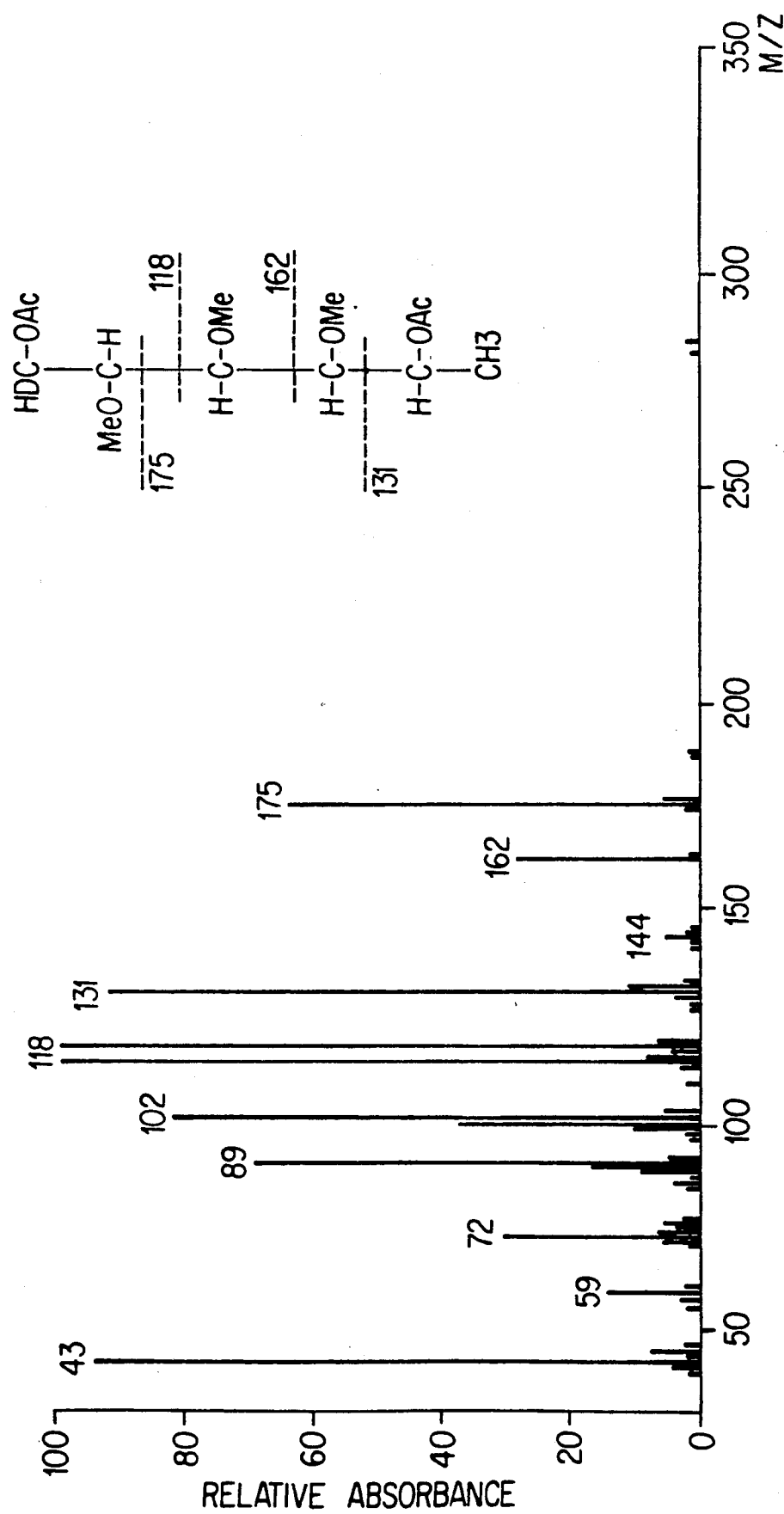
FIGS. 3–10 shows mass spectra for the peaks 1–8 respectively in the total ion chromatograph of FIG. 2, showing the sites in the molecule indicated by the mass spectrum peaks.
Figure 4:
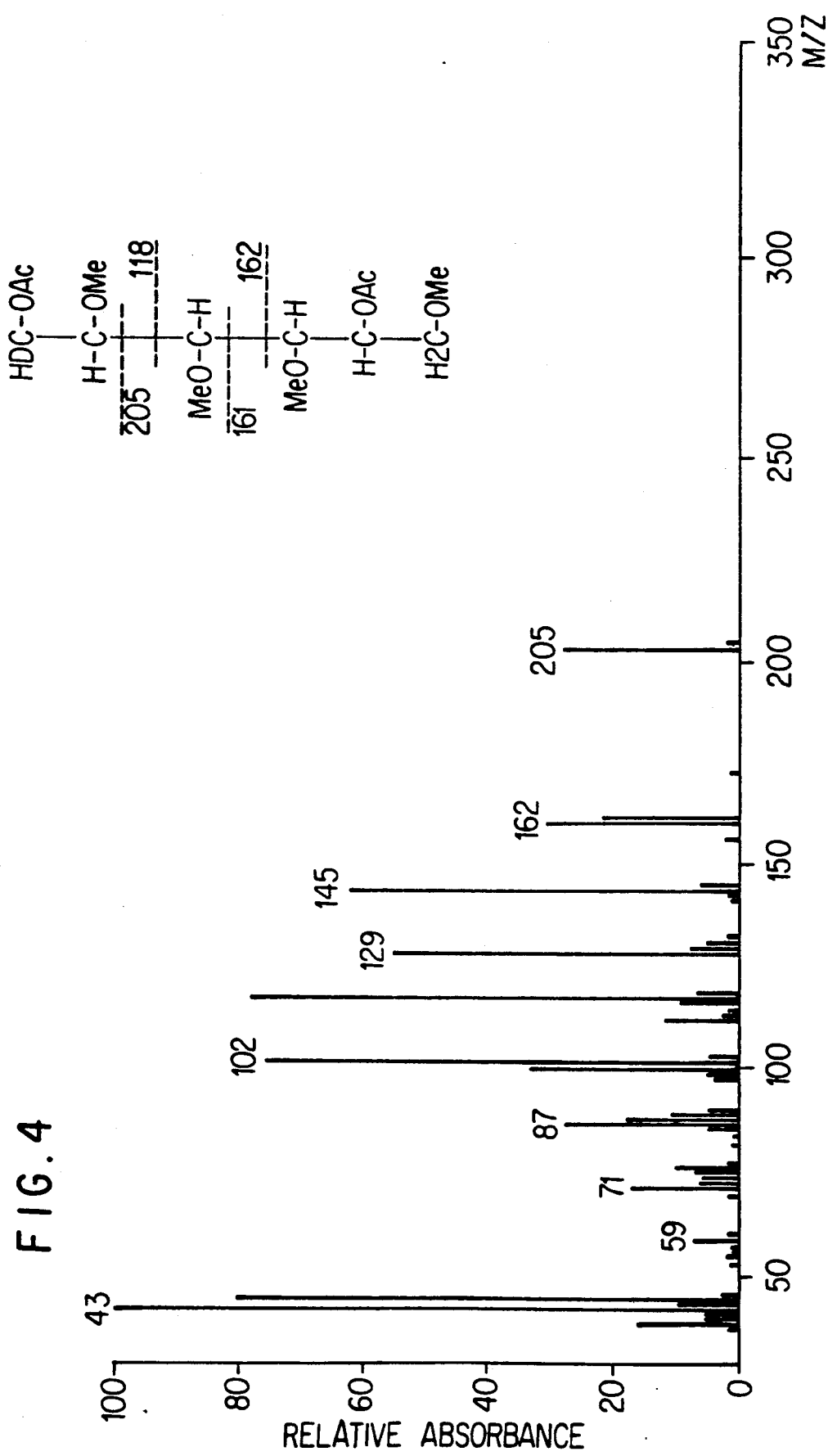
Figure 5:
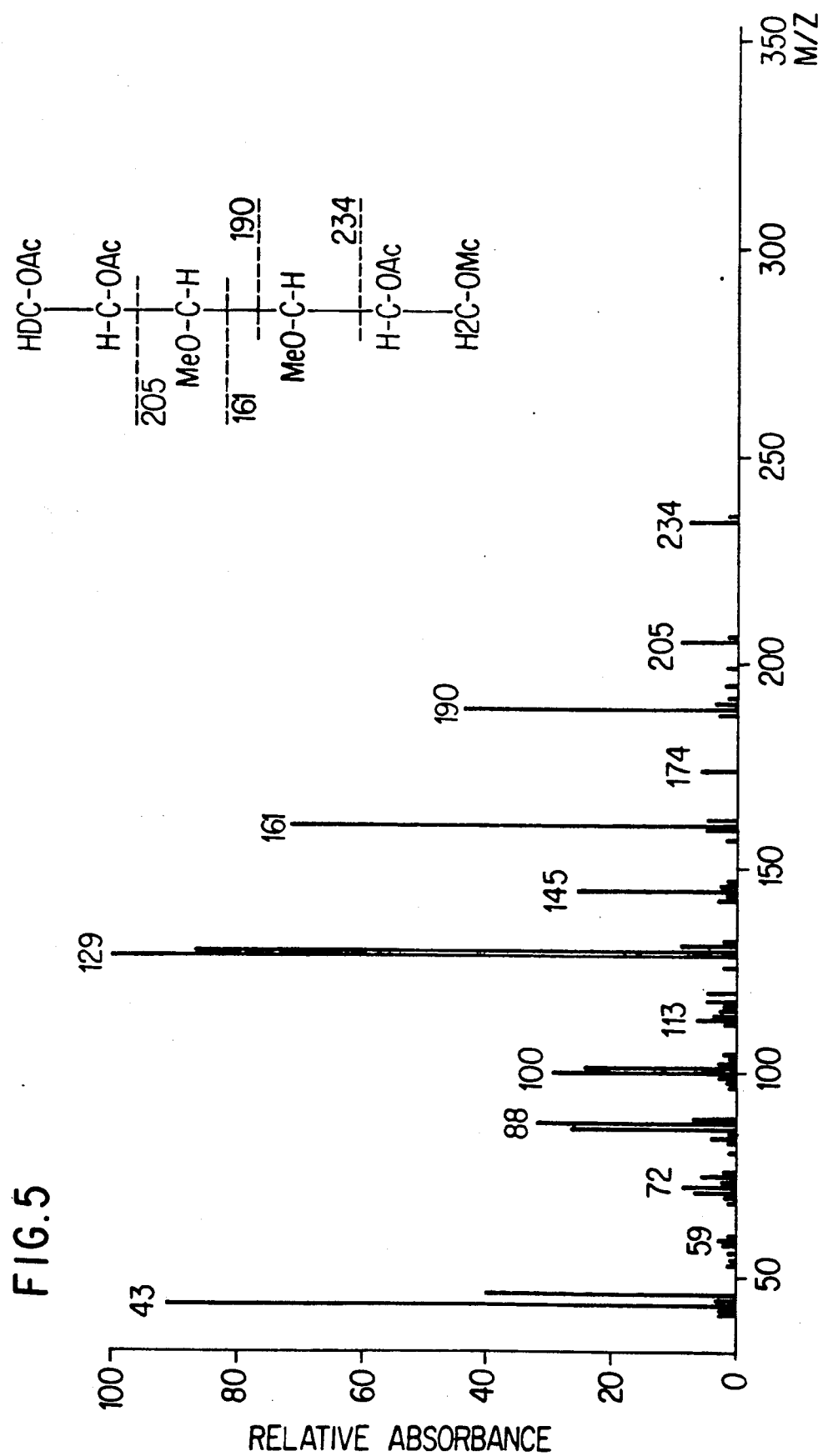
Figure 6:
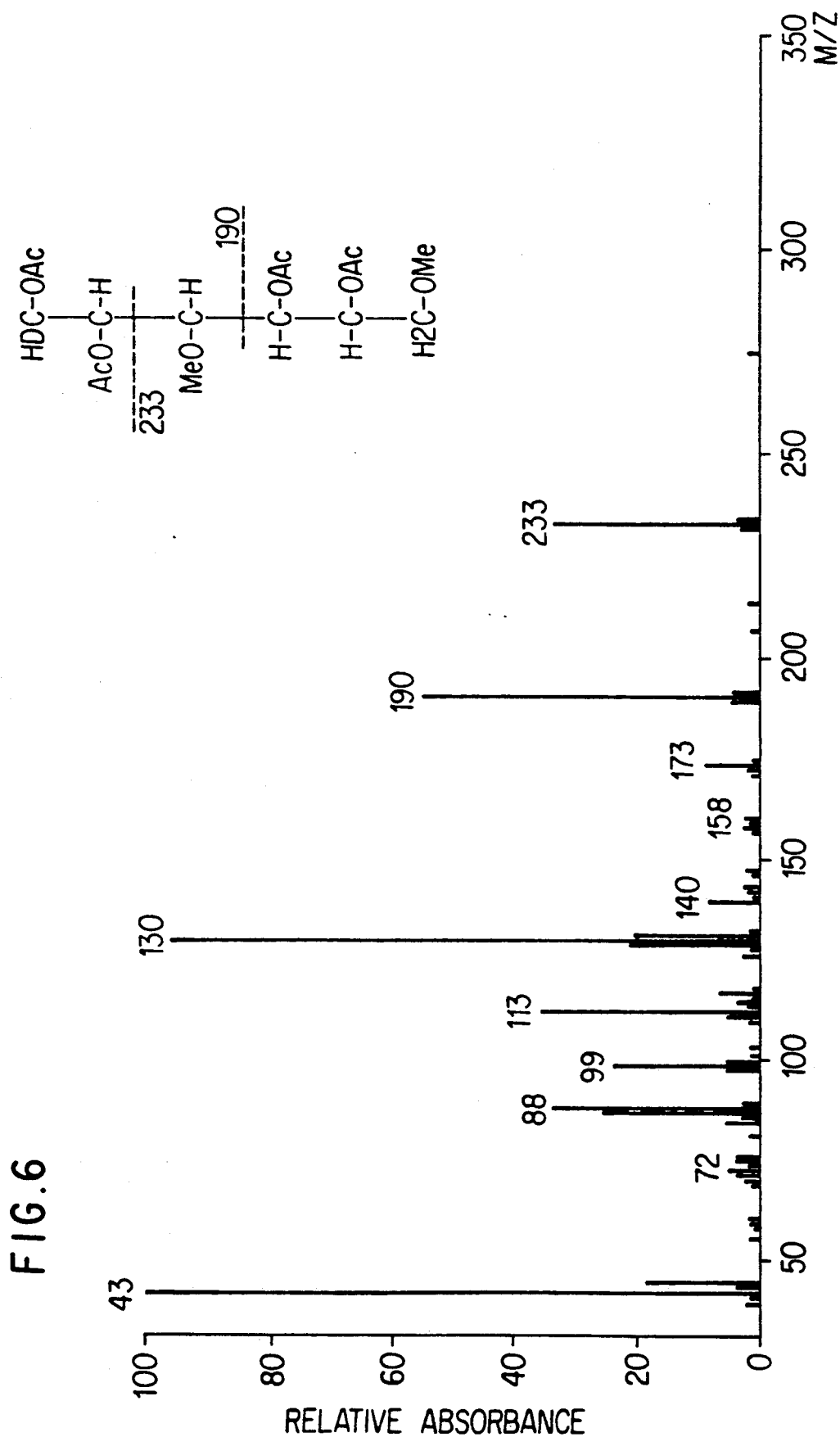
Figure 7:
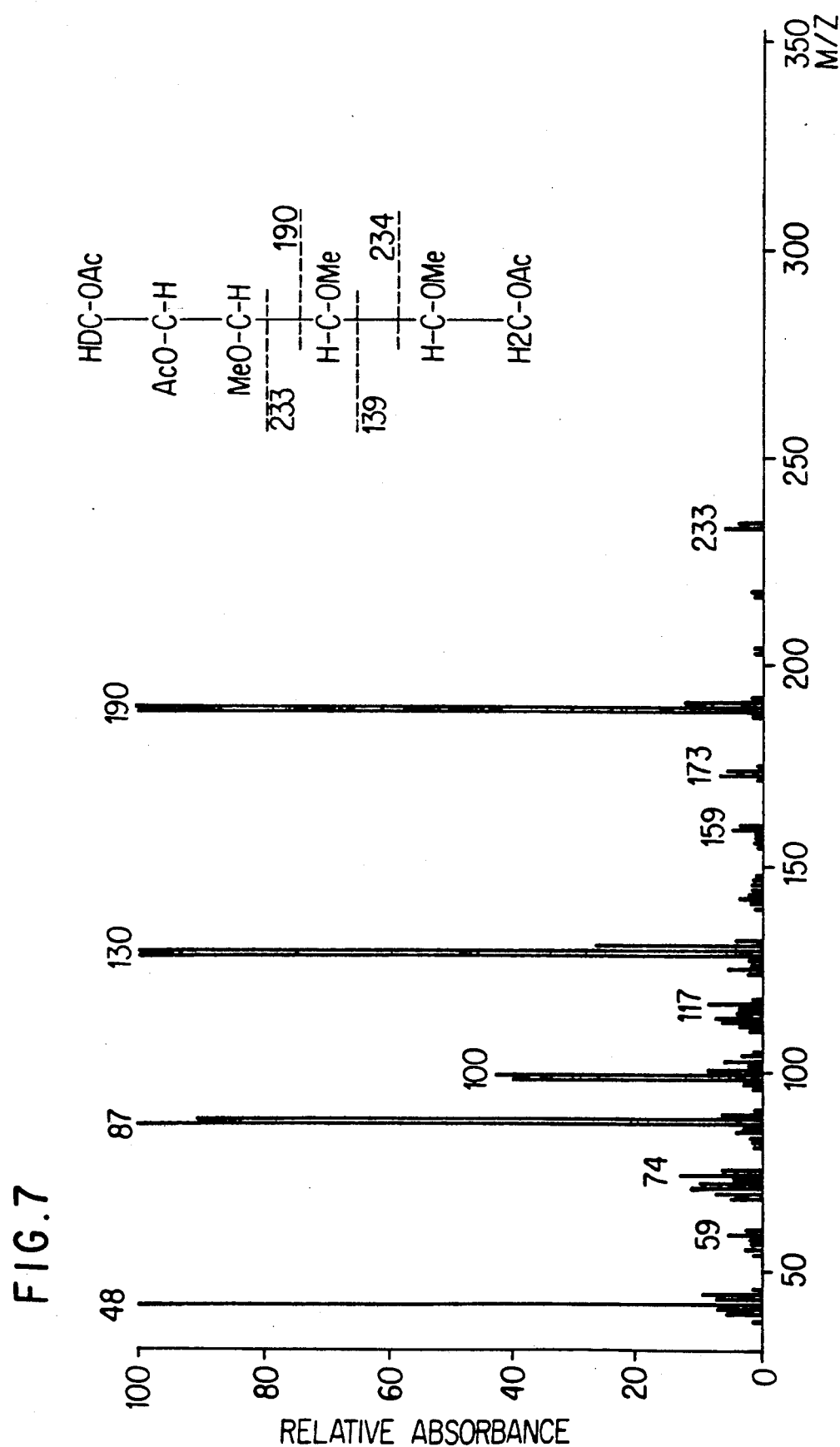
Figure 8:
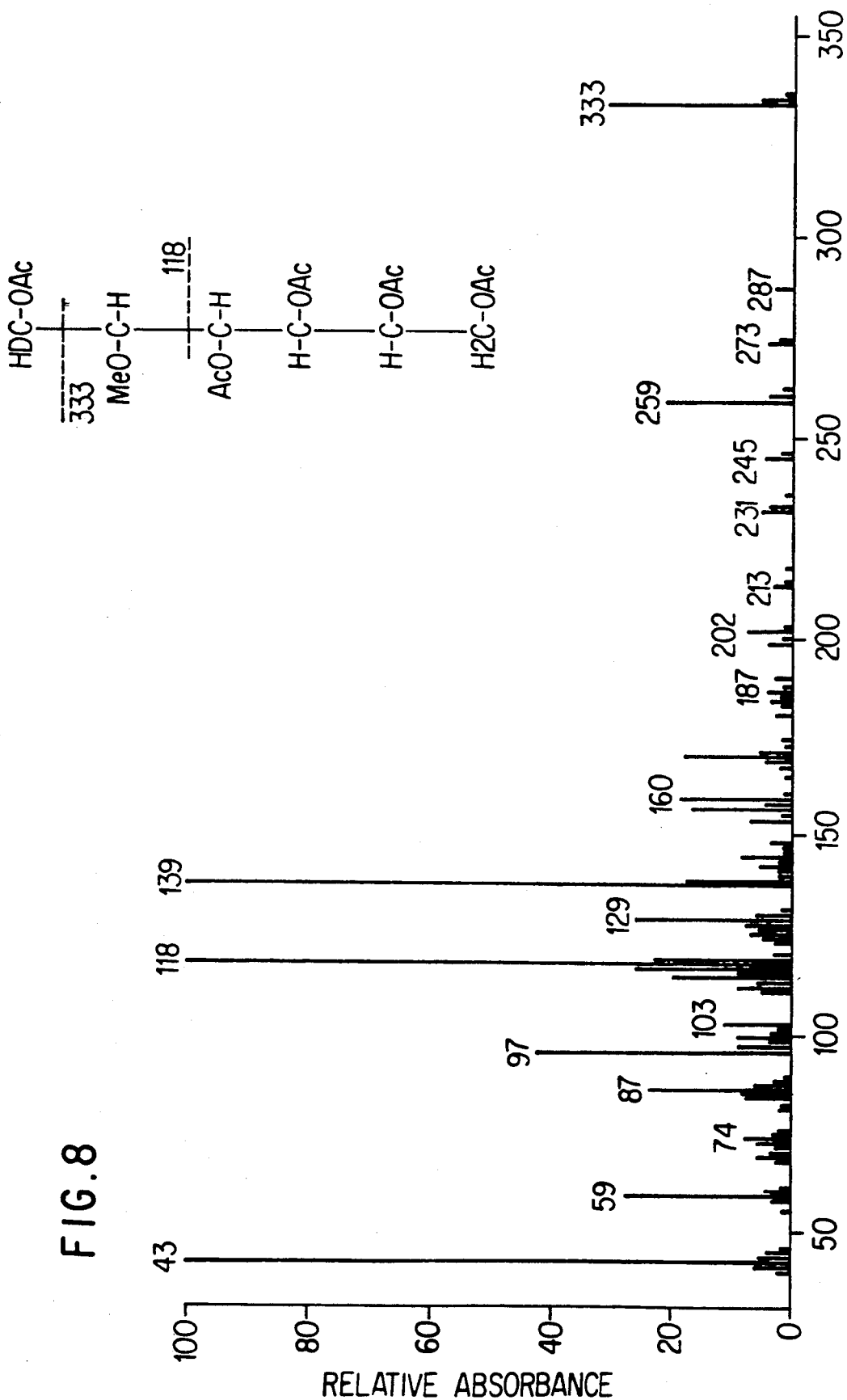
Figure 9:
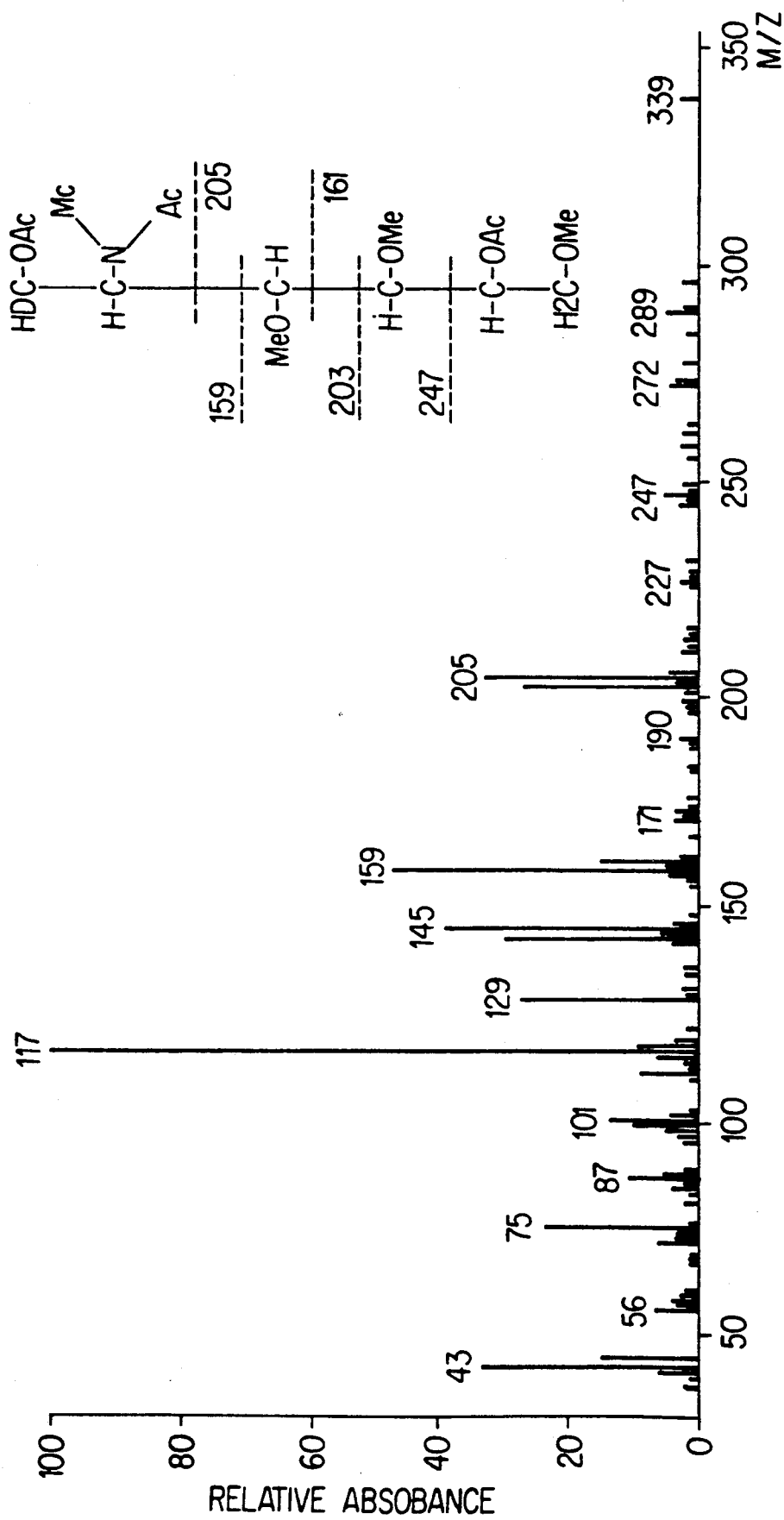
Figure 10:
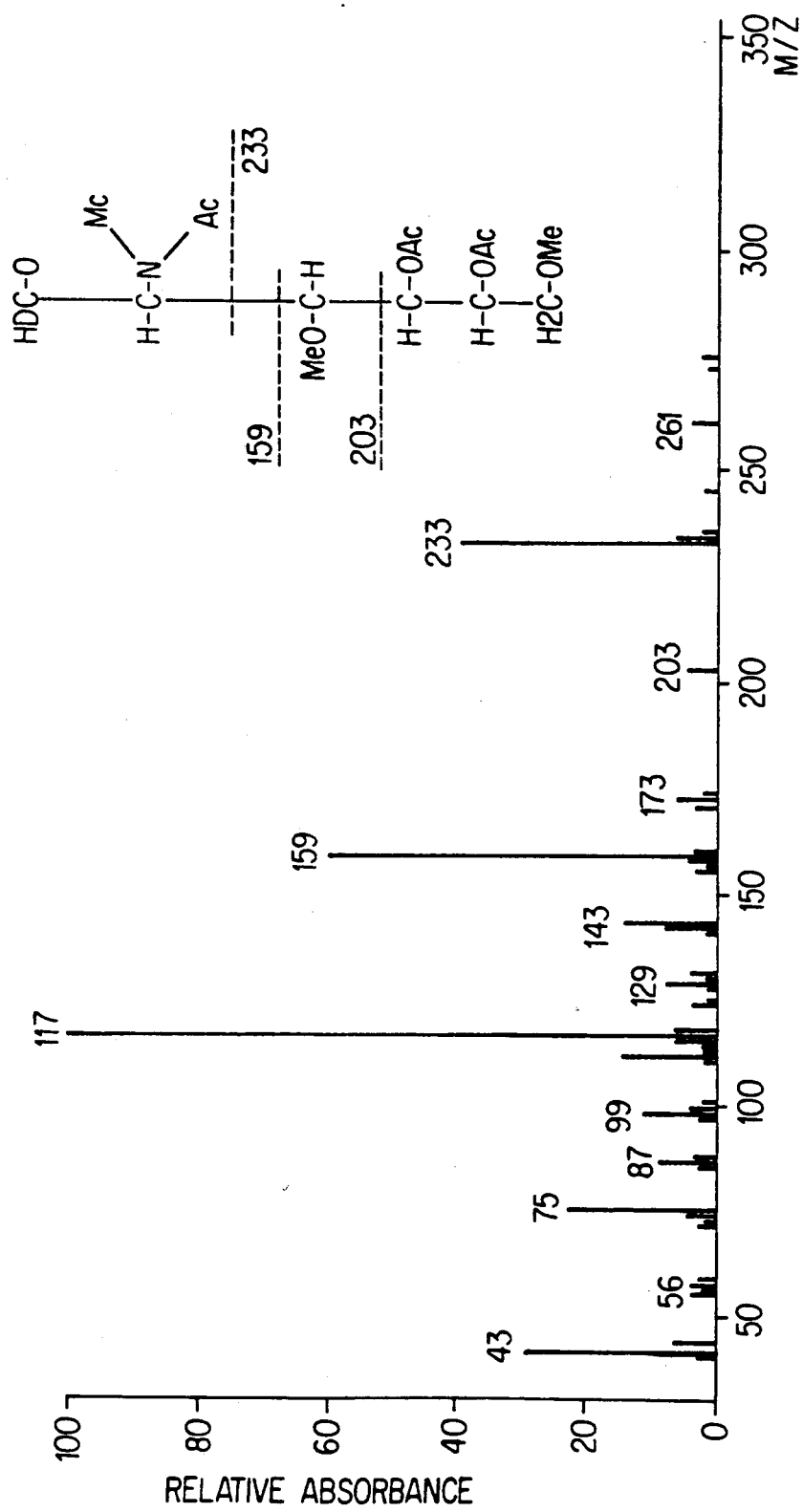

The total ion chromatograph of the methylation analysis is given in FIG. 2, and mass spectra for the peaks 1-8 indicated by the total ion chromatograph are shown in FIGS. 3-10, in which sites in the molecule indicated by the mass spectrum peaks are shown. The relations between the peaks 1-8 detected in the total ion chromatograph of the methylation analysis and the chemical shift detected by $^1$H-NMR analysis are shown in Table 3.

TABLE 3

| Partially methylated alditol acetate | Peak No. in the total ion chromatograph | $^1$H-NMR Chemical shift (Anomeric proton) |
|---|---|---|
| Fucitol | | |
| 2,3,4-Tri-O-methyl | 1 | Fuc α1-(6), α1-(2) |
| Galactitol | | |
| 2,3,4,6-Tetra-O-methyl | 2 | Gal-8',6',8 |
| 3,4,6-Tri-O-methyl | 3 | Gal-6 |
| Mannitol | | |
| 3,6,-Di-O-methyl | 4 | Man-4 |
| 3,4,-Di-O-methyl | 5 | Man-4' |
| 2-Mono-O-methyl | 6 | Man-3 |
| 2-N-Methylacetamido- | | |
| 2-deoxyglucitol | | |
| 3,4,6-Tri-O-methyl | 7 | GlcNAc-bisect |
| 3,6-Di-O-methyl | 8 | GlcNAc-7', 5', 7, 5, 2 |

The sugar chain of the present invention is useful as an agent for treating cancers, rheumatism, and the like, as well as immunoactivating agent. Furthermore, the antibody for the sugar chain of the present invention is useful for the treatment and diagnosis of diseases such as cancers, rheumatism, and the like.

Obviously, numerous modifications and variations of the present invention are possible in light of the above teachings. It is therefore to be understood that within the scope of the appended claims, the invention may be practiced otherwise than as specifically described herein.

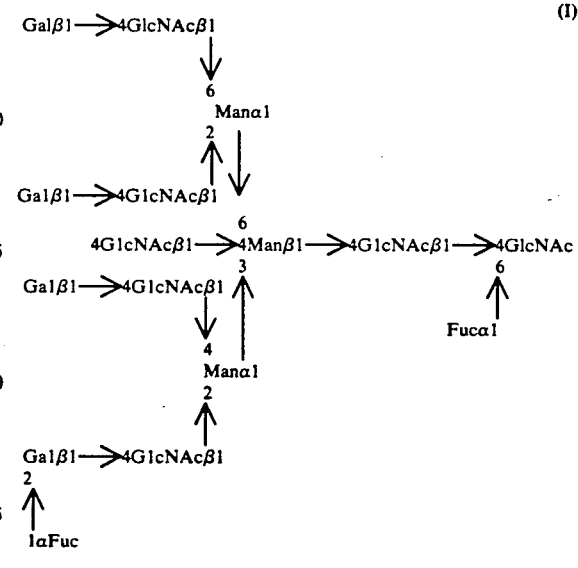

What is claimed is:

1. A sugar chain of the formula (I):